United States Patent [19]

De Decker et al.

[11] Patent Number: 4,804,754

[45] Date of Patent: Feb. 14, 1989

[54] PREPARATION OF CAPROLACTAM FROM CYCLOHEXANONE OXIME BY BECKMANN REARRANGEMENT

[75] Inventors: Emile De Decker, Hoboken; Jozef Oostvogels, Schoten; Gerard van Wauwe, Edegem, all of Belgium; Gerald Neubauer, Weinheim, Fed. Rep. of Germany

[73] Assignee: BASF Aktiengesellschaft, Ludwigshafen, Fed. Rep. of Germany

[21] Appl. No.: 130,949

[22] Filed: Dec. 10, 1987

[30] Foreign Application Priority Data

Dec. 11, 1986 [DE] Fed. Rep. of Germany ....... 3642314

[51] Int. Cl.$^4$ .................. C07D 201/04; C07D 201/16
[52] U.S. Cl. ..................................... 540/535; 540/540
[58] Field of Search .......................... 540/535; 340/540

[56] References Cited

U.S. PATENT DOCUMENTS

| | | | |
|---|---|---|---|
| 2,221,369 | 11/1940 | Cass | 540/535 |
| 2,313,026 | 3/1943 | Schlack | 340/535 |
| 3,145,198 | 8/1964 | Mordidelli et al. | 540/540 |
| 3,544,562 | 12/1970 | Schultze et al. | 540/535 |
| 3,553,204 | 1/1971 | Gehring et al. | 540/535 |
| 3,914,217 | 10/1975 | Smith | 540/535 |
| 3,953,438 | 4/1976 | Smith | 540/535 |

FOREIGN PATENT DOCUMENTS 4839949 11/1973 Japan .................. 540/532

OTHER PUBLICATIONS

Chem. Abstracts, Apr. 15, 1974, 82130f.

*Primary Examiner*—Robert T. Bond
*Attorney, Agent, or Firm*—Keil & Weinkauf

[57] ABSTRACT

Caprolactam is prepared in a process comprising
(a) a Beckmann rearrangement of cyclohexanone oxime with oleum at from 70° to 130° C. in one or more rearrangement stages, and
(b) aftertreatment of the reaction mixture obtained from the rearrangement stage in a delay zone at from 70° to 110° C. for from 10 to 600 minutes.

4 Claims, No Drawings

PREPARATION OF CAPROLACTAM FROM CYCLOHEXANONE OXIME BY BECKMANN REARRANGEMENT

The present invention relates to a process for preparing caprolactam from cyclohexanone oxime by Beckmann rearrangement using oleum.

Japanese patent application No. 48-39,949 discloses a process where cyclohexanone oxime is reacted in oleum in a plurality of reaction zones connected in series, not less than 70% of the oleum being charged to the first reaction zone and the cyclohexanone oxime being added distributed over the individual reaction zones. In a process described in U.S. Pat. No. 3,953,438, cyclohexanone oxime is reacted with oleum in two circulation zones in series, the larger portion of the cyclohexanone oxime being added to the first reaction zone and the smaller portion to the second reaction zone, and all of the oleum being charged to the first reaction zone. It is true that using the prior art processes the permanganate absorption number is substantially reduced, yet it is has been found that the quality of caprolactam thus produced does not meet today's requirements.

It is an object of the present invention to provide a process of preparing caprolactam from cyclohexanone oxime by Beckmann rearrangement using oleum, wherein the caprolactam thus prepared is distinguished not only by a lower permanganate absorption number but also by a lower UV number and a reduced octahydrophenazine content.

We have found that this object is achieved in a process for preparing caprolactam by Beckmann rearrangement of cyclohexanone oxime with oleum at from 70° to 130° C. in one or more rearrangement stages by keeping the reaction mixture obtained from the rearrangement in a delay zone at from 70° to 110° C. for from 10 to 600 minutes.

The novel process has the advantage that the quality of the caprolactam produced is improved in a simple manner, and more particularly that not only the permanganate absorption number but also the UV number and the octahydrophenazine content are reduced.

The starting point is, in general, cyclohexanone oxime in the form of a liquid melt, for example at from 80° to 95° C. The cyclohexanone oxime melt generally has a water content of from 0 to 7%, advantageously from 3.5 to 6% by weight. Cyclohexanone oxime is rearranged with oleum. Advantageously, the oleum used has a sulfur trioxide content of from 24 to 35% by weight. Preferably, from 1.1 to 1.8 kg of oleum are used per kg of cyclohexanone oxime. The rearrangement is carried out at from 70° to 130° C., in particular from 108° to 118° C.

The reaction is carried out for example in a circulating mixture of caprolactam and sulfuric acid. Cyclohexanone oxime melt and, separately therefrom, oleum are introduced via dividers. In the circulating mixture a weight ratio of sulfuric acid:caprolactam of from 1.0 to 2.0 and a free sulfur trioxide content of from 1.0 to 14% by weight are maintained. Cooling is employed to maintain a temperature of from 70° to 130° C., the pump rate varying from 40 to 150 times the volume of the circulation system per hour. Upstream of where the cyclohexanone oxime and oleum are added, a mixture of sulfuric acid and caprolactam is removed at a rate commensurate with that of the addition of cyclohexanone oxime and oleum. The average residence time in the circulation system ranges advantageously from 30 to 120 minutes.

In a preferred embodiment, the rearrangement is carried out in a plurality, for example two to four, stages connected in series. Each of these stages is charged with cyclohexanone oxime, advantageously at a rate decreasing from stage to stage, while not less than 70%, in particular not less than 90%, preferably all of the oleum required is charged into the first stage. In a two-stage rearrangement, for example, the first stage is charged with from 60 to 95 parts by weight of cyclohexanone oxime and all of the oleum and is maintained under a weight ratio of sulfuric acid:caprolactam from 1.0 to 2.0, and a free sulfur trioxide content of 2.0 to 14.0% and at from 70° to 130° C. The reaction mixture thus obtained, which consists essentially of sulfuric acid, caprolactam and sulfur trioxide, is transferred at the rate of addition of the oleum and cyclohexanone oxime into a second stage, where the remaining 5 to 40 parts by weight of cyclohexanone oxime are added and a weight ratio of sulfuric acid:caprolactam in the circulating mixture of from 1.0 to 1.5 and a free sulfur trioxide content of from 1.0 to 6% by weight are maintained. The circulating reaction mixture is maintained at from 70° to 130° C.

According to the invention, the reaction mixture obtained from the rearrangement is maintained prior to neutralization in a delay zone, for example a stirred kettle of in particular an elongated structure, for example a tube, for from 10 to 600 minutes, in particular from 15 to 180 minutes, at from 70° to 110° C., in particular from 90° to 100° C.

The reaction mixture thus obtained, which consists essentially of caprolactam, sulfuric acid, residual sulfur trioxide and by-products, is neutralized with ammonia. Advantageously, the reaction mixture is charged in a circulation system into a 35 to 45% strength by weight aqueous ammonium sulfate solution and mixed therewith, while gaseous ammonia is passed in to neutralize the mixture to pH 4–5. The resulting precipitate of crude lactam is separated from the saturated ammonium sulfate solution, for example by decanting, and extracted with benzene. After the benzene has been separated off, the caprolactam is purified by distillation under reduced pressure.

The caprolactam obtainable by the process according to the invention is distinguished by improved purity, in particular reduced UV number and octahydrophenazine content.

The process of the invention is illustrated in the following examples.

COMPARATIVE EXAMPLE

Procedure without delay zone

In a circulation system of 10 m$^3$ capacity in total, comprising connection lines, pump, coolers and degassing/overflow vessel, a circulation rate of 70 times the circulation system volume per hour was maintained. The entire amount of cyclohexanone oxime was added as a melt at 85° C. via a divider.

The cyclohexanone oxime used had a water content of 4.2% by weight. At the same time, oleum containing 32% by weight of SO$_3$ was added in a second divider. The ratio of oleum:oxime was 1.17 kg/kg. The temperature upstream of the dividers was 115° C. The average residence time in the circulation system was about 60 minutes. The quantities introduced into the reaction cycle reemerged as reaction products from the circulation system in the overflow vessel and were mixed in a second circulation system with approximately 40 to 43% strength aqueous ammonium sulfate solution and neutralized with gaseous ammonia to pH 4.6. Crude lactam precipitated out of the almost saturated ammonium sulfate solution and was separated off. The water-containing crude lactam (the water content being approximately 30%) was prepurified by extraction with benzene, and the extract lactam thus formed was subjected to a final purification by vacuum distillation to give pure lactam.

The following parameters were measured in the pure lactam:
  Permanganate titration number: 2.6
  Permanganate absorption number: 3.6
  UV number: 5.0
  Absorbance 290 nm/10 cm pathlength: 0.45
  OHP (octahydrophenazine) ppm: 0.8

EXAMPLE

Procedure with delay zone

In the same circulation system as described in the Comparative Example, cyclohexanone oxime was rearranged under the conditions stated there. The resulting reaction product was then delayed in a separate vessel at 95° C. for 120 minutes and subsequently worked up as described to give pure lactam.

The following parameters were measured in the pure lactam:
  Permanganate titration number: 2.2
  Permanganate absorption number: 3.1
  UV number: 2.5
  Absorbance 290 nm/10 cm pathlength: 0.3
  OHP (octahydrophenazine) ppm: 0.5

We claim:
1. A process for preparing caprolactam, comprising
   (a) a Beckmann rearrangement of cyclohexanone oxime with oleum at from 108° to 118° C. in one or more rearrangement stages, and
   (b) maintaining the reaction mixture obtained from the rearrangement stage in a dwelling zone at from 90° to 100° C. for from 10 to 600 minutes.
2. The process of claim 1, wherein the rearrangement is carried out in two or three rearrangement stages connected in series.
3. The process of claim 1, wherein a total amount of oleum and from 60 to 95 parts by weight of cyclohexanone oxime are added to the first rearrangement stage and from 5 to 40 parts by weight of cyclohexanone oxime to the subsequent rearrangement stage or stages.
4. The process of claim 1, wherein a residence time of from 15 to 180 minutes is maintained in the dwell zone.

* * * * *